United States Patent [19]
Castaldi et al.

[11] Patent Number: 4,618,697
[45] Date of Patent: * Oct. 21, 1986

[54] PROCESS FOR PREPARING ALPHA-ARYLALKANOIC ACIDS

[75] Inventors: Graziano Castaldi, Briona; Claudio Giordano, Vicenza, both of Italy

[73] Assignee: Zambon SpA, Vicenza, Italy

[*] Notice: The portion of the term of this patent subsequent to Aug. 13, 2002 has been disclaimed.

[21] Appl. No.: 576,711

[22] Filed: Feb. 3, 1984

Related U.S. Application Data

[63] Continuation-in-part of Ser. No. 520,131, Aug. 3, 1983, Pat. No. 4,535,166.

[30] Foreign Application Priority Data

Mar. 7, 1983 [IT] Italy .............................. 19930 A/83

[51] Int. Cl.$^4$ .................................................. C07C 69/76
[52] U.S. Cl. ...................................... 560/56; 560/55; 560/105; 562/465; 562/466; 562/496
[58] Field of Search ........................... 560/56, 55, 105; 562/465, 466, 496

[56] References Cited

U.S. PATENT DOCUMENTS 4,539,420  9/1985  Tsuchihashi et al. ................. 560/56

FOREIGN PATENT DOCUMENTS 3012837  4/1978  Japan ................................... 560/105

Primary Examiner—Paul J. Killos
Attorney, Agent, or Firm—Cushman, Darby & Cushman

[57] ABSTRACT

This invention relates to a process for preparing an alpha-arylalkanoic acid or salt thereof which comprises the rearrangement of an alpha-halo-alkylarylketal in neutral or slightly alkaline conditions, in the presence of a dipolar aprotic diluent and of a protic substance having a high dielectric constant, and the subsequent hydrolysis of the thus obtained ester.

8 Claims, No Drawings

PROCESS FOR PREPARING ALPHA-ARYLALKANOIC ACIDS

This application is a continuation-in-part of our co-pending application Ser. No. 520,131 filed on Aug. 3, 1983, now U.S. Pat. No. 4,535,166.

This invention relates to a process for preparing an alpha-arylalkanoic acid or salt thereof which comprises the rearrangement of an alpha-chloro (or bromo)-alkylarylketal in neutral or slightly alkaline conditions, in the presence of a dipolar aprotic diluent and of a protic substance having a high dielectric constant, and the subsequent hydrolysis of the thus obtained ester.

The European Patent Application No. 34 871 describes a process for preparing esters of alpha-arylalkanoic acids via rearrangement of alpha-halo alkylarylketals in the presence of a Lewis acid. The disadvantages of this process consist in the fact that the reaction must be carried out in an anhydrous medium and that the more effective Lewis acids are the salts of toxic heavy metals; consequently there is a need for a careful purification when the final product is intended for pharmaceutical use.

Furthermore the Lewis acids incline to interact with the oxygen atoms of the ketal group and, consequently, to form by-products whose amount ranges in accordance with the nature of the alpha-halo-alkylarylketal and of the Lewis acid which are used.

The European Patent Application No. 48 136 describes a process for preparing alpha-arylalkanoic acids wherein an alpha-sulfonyloxyketal undergoes hydrolysis. This process lays on the prejudice that the halogen atom is not sufficiently labile to promote the rearrangement in the absence of a catalyst having affinity for halogen whereas it was well known that the sulfonyloxy-groups, e.g. tosyloxy and mesyloxy, are sufficiently labile to dissociate from the substrate upon contact with a protic-polar medium.

Despite the apparent easy of the last step, this process is complex and cumbersome owing to the fact that at first an alpha-halo-ketone is reacted with an alkali metal alkoxide to afford an alpha-hydroxyketal which is then treated with an O-sulfonylating agent to form the corresponding alpha-sulfonyloxyketal and finally the alpha-sulfonyloxyketal is submitted to hydrolysis. The number of steps involved and the difficulties inherent in carrying out on a large scale some of the steps, leave room for a more simple and economical process.

In our co-pending U.S. application Ser. No. 520,131 we describe a process for the preparation of alpha-arylalkanoic acids which comprises the rearrangement of an alpha-halo-alkyl-arylketal in neutral or slightly alkaline conditions and in the presence of a polar protic medium consisting of water, an alcohol or a mixture thereof.

We have now found that the rearrangement reaction may also be carried out with very satisfactory results in neutral or slightly alkaline conditions in the presence of a dipolar aprotic diluent and of a protic substance having a high dielectric constant thus avoiding the detour depicted in the European Patent Application No. 48 136 as well as disadvantages inherent in the process described in the European Patent Application No. 34 871.

More particularly, the process according to this invention comprises the rearrangement of an alpha-chloro (or bromo)-alkylarylketal in neutral or slightly alkaline conditions, in the presence of a dipolar aprotic diluent and of a protic substance having a high dielectric constant, and the subsequent hydrolysis of the thus obtained ester.

The process object of the invention may be represented by the following reactions:

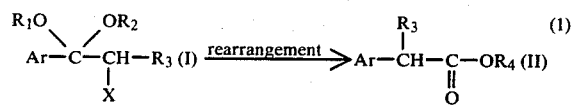

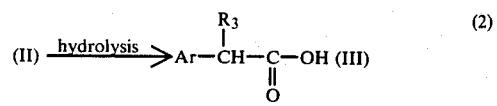

wherein

Ar is an aromatic radical selected from the group comprising (a) phenyl substituted by one or two substituents selected from the group comprising halogen, 1–6 C alkyl, 1–4 C alkoxy, 2–4 C alkenyloxy, difluoromethoxy, phenyl, phenoxy, dichlorophenoxy, dichloroanilino, benzoyl, indolinyl, dihydropyrrolyl, thienoyl, (b) naphthyl substituted by one or two substituents selected from the group comprising halogen and 1–4 C alkoxy, (c) pyrrolyl substituted by one or two radicals selected from the group comprising 1–4 C alkyl and 1–4 C alkylphenyl, (d) chloro-carbazolyl, (e) benzoxazolyl substituted by one chlorophenyl radical, (f) thiazolyl substituted by one or two radicals selected from the group comprising phenyl and chlorophenyl, and (g) thienyl, $R_1$ and $R_2$, independently from each other, are a saturated or unsaturated, straight or branched alkyl radical having from 1 to 12 C atoms, or when taken together are a saturated or unsaturated straight or branched alkylene radical having from 2 to 12 C atoms, X is chlorine or bromine, $R_3$ is hydrogen, alkyl having from 1 to 6 carbon atoms or cycloalkyl having from 3 to 7 carbon atoms, $R_4$ is a saturated or unsaturated, straight or branched alkyl radical having from 1 to 12 carbon atoms which may be optionally substituted by a chlorine or bromine atom, a hydroxy or acetoxy group.

Usually $R_4$ is an alkyl when $R_1$ and $R_2$ are alkyls and is a substituted alkyl when $R_1$ and $R_2$ together form an alkylene radical, the specific substituent of $R_4$ depends on the components of the reaction mixture.

Specific examples of useful starting products (ketals) include the compounds of formula I wherein Ar is 4-methoxy-phenyl, 4-isobutylphenyl, 4-chloro-phenyl, 6-methoxy-2-naphthyl; $R_1$ and $R_2$ are methyl or $R_1$ and $R_2$ together are —$CH_2$—$CH_2$—, —$CH_2$—$CH_2$—$CH_2$—, —$CH_2$—$C(CH_3)_2$—$CH_2$—; $R_3$ is hydrogen or $C_1$–$C_6$ alkyl; X is chlorine or bromine.

The neutral or slightly alkaline condition is obtained by adding to the reaction mixture a buffer or a weak base either organic or inorganic or mixture thereof. Examples of typical compounds are the aliphatic and the aromatic tertiary amines and the alkali and alkaline earth metal salts of organic and inorganic acids such as sodium bicarbonate, calcium carbonate, potassium acetate, triethylamine, methylpiperidine, methyl-pyrrolidine and dimethylaniline. The dipolar aprotic diluents useful in the process object of the invention include: dimethylformamide, dimethylsulphoxide, hexamethylfosforotriamide, N-methyl-pyrrolidone, dimethylacetamide, N-methyl-morpholine, O-alkylated polyglycols, sulpholane and mixtures thereof.

The protic substances having a high dielectric constant (if solid, when in solution) useful in the process object of the invention include: water, urea, thiourea, formamide, acetamide, benzamide, phenols, N-methyl-formamide, N-methyl-acetamide, N,N'-dimethyl-urea and mixtures thereof. Formamide, due to its good solubilizing properties with respect to the ketals of formula I, does not need the presence of a dipolar aprotic diluent.

The amount of dipolar aprotic diluent to be used depends on the relative solubility of the selected ketal. A complete solubility of the ketal in the reaction mixture is not an essential feature.

In general an amount of dipolar aprotic diluent sufficient for dissolving about 10% by weight of the ketal is sufficient.

Also the amount of the protic substance having a high dielectric constant is not a critical feature. With respect to the ketal, the protic substance may be used in catalytic amounts up to equimolecular amounts or in excess. With respect to the dipolar aprotic diluent, the amount of protic substances may vary in a wide range.

For practical purposes the ratio dipolar diluent: protic substance is comprised between 100:1 and 1:1 by volume (or by weight when one of the compounds is a solid), the preferred range being from 20:1 to 1:1. Higher amounts of the protic substance generally increase the reaction rate.

The reaction temperature is comprised between 80° C. and 200° C.

The duration of the reaction depends on various features such as the reactivity of the selected ketal, its solubility in the reaction medium, the selected polar aprotic diluent and its amount, the selected protic substance having a high dielectric constant and its amount.

Generally the reaction is complete in a period of time ranging from 30 minutes to 36 hours.

At the end of the rearrangement reaction the mixture is worked up according to conventional methods to isolate the ester (II) thus obtained which is then subjected to hydrolysis according to conventional procedures thus affording the desired arylalkanoic acid (III) in high yields and with high purity.

In a practical embodiment the process object of the invention is carried out by introducing in the reactor the ketal of formula I, an amount of dipolar aprotic diluent sufficient for dissolving at least partially the ketal, the protic substance having a high dielectric constant and an amount of a buffer or of a weak base sufficient to ensure a neutral or slightly alkaline pH.

The reaction mixture is heated while stirring to a temperature comprised between 80° C. and 200° C.

The course of the reaction is followed according to conventional methods (e.g. TLC, GLC or Infra-red spectroscopy).

At the end of the rearrangement reaction, the mixture is poured into water.

The ester (II) is separated by extraction and isolated.

The hydrolysis of the ester is carried out according to conventional procedures, for example by acid hydrolysis or preferably by treatment with an aqueous alkali metal hydroxide to afford the corresponding carboxylic acid salt from which, by treatment with a strong mineral acid, the free acid is obtained.

The ketals of formula I are known compounds or may be easily obtained by ketalization of the corresponding alpha-haloalkyl-aryl-ketones.

Examples of methods suitable for preparing alpha-haloalkyl-arylketals comprise the use of an acid catalyst such as p-toluene-sulphonic acid (J. Org. Chem. 21, 1366, (1956); ibidem, 22, 662, (1957); Synthesis 23, (1974)), active montmorillonite (Bull. Soc. Chim. France, 2558, (1975)), $BF_3$ etherate (Bull. Soc. Chim. France 1763, (1975)) and citric acid (U.S. Pat. No. 3,936,398). An improvement to the last method contemplates the use of citric acid in the presence of hydroquinone which acts as polymerization inhibitor (Bull. Soc. Chim. France, 1973, (1975)).

The water generated in the course of the reaction is removed by azeotropic distillation with suitable solvents such as benzene, toluene, cyclohexane and the like or by means of a dehydrating agent such as anhydrous $CuSO_4$, a trialkylorthoformate, molecular sieves and the like (Synthesis, 501, (1981)).

Other known methods for preparing the ketals are trans-ketalization, the reaction of a ketone with an alcohol in the presence of a ketal such as 2,2-dimethoxypropane and an acid catalyst (J. Org. Chem. 25, 521 (1960)) and the reaction of an alcohol with a suitable enol-ether in the presence of an acid catalyst (Bull. Soc. Chim. France, 264, (1979)).

The known alpha-halo-alkylarylketals include:
2-bromo-1,1-dimethoxy-1-(6'-methoxy-2'-naphthyl)-propane,
2-bromo-1,1-dimethoxy-1-(4'-isobutylphenyl)-propane,
2-(1'-bromoethyl)-2-(6'-methoxy-2'-naphthyl)-1,3-dioxane,
2-(1'-bromoethyl)-2-(6'-methoxy-2'-naphthyl)-1,3-dioxolane.

Examples of not-yet described alpha-halo-alkylarylketals which are prepared according to known techniques are:
2-bromo-1,1-dimethoxy-1-(4'-methoxyphenyl)-propane
$^1$H-NMR (60 MHz) ($CDCl_3$-TMS) delta (ppm): 1.45 (d, 3H); 3.15 (s, 3H); 3.8 (s, 3H); 4.5 (q, 1H); 6.85–7.6 (m, 4H).
2-(1'-bromoethyl)-5,5-dimethyl-2-(6'-methoxy-2'-naphthyl)-1,3-dioxane, m.p. 89°–90° C.
2-(1'-bromoethyl)-2-(4'-methoxyphenyl)-1,3-dioxane
$^1$H-NMR (60 MHz) ($CDCl_3$-TMS) delta (ppm): 1.65 (d, 3H); 3.6–4 (m, 6H); 3.85 (s, 3H); 4.1 (q, 1H); 7–7.7 (m, 4H).
2-(1'-bromoethyl)-2-(6'-methoxy-2'-naphthyl)-1,3-dioxane $^1$H-NMR (60 MHz) ($CDCl_3$-TMS) delta (ppm): 1.20 (m, 2H); 1.68 (d, 3H); 3.90 (m, 4H); 3.96 (s, 3H); 4.30 (q, 1H); 7.12–7.98 (m, 6H).
2-bromoethyl-5-(2'-butyl)-5-methyl-2-(4'-methoxyphenyl)-1,3-dioxane.
2-(1'-bromoethyl)-5,5-dimethyl-2-(4'-isobutylphenyl)-1,3-dioxane, b.p. 135°–138° C. (0.6 mmHg)
2-(1'-bromoethyl)-5,5-dimethyl-2-(5'-bromo-6'-methoxy-2'-naphthyl)-1,3-dioxane, m.p. 143°–145° C.
2-(1'-bromoethyl)-5,5-dimethyl-2-(2'-thienyl)-1,3-dioxane, b.p. 78°–80° C. (0.5 mmHg).
2-(1'-bromoethyl)-2-(4'-methoxyphenyl)-1,3-dioxolane
$^1$H-NMR (60 MHz) ($CDCl_3$-TMS) delta (ppm): 1.6 (d, 3H), 3.8 (s, 3H); 3.8–4.2 (m, 4H); 4.4 (q, 1H); 6.85–7.6 (m, 4H).

Other useful new alpha-halo-alkylarylketals of formula I are those where $R_1$ and $R_2$ together are a straight or branched unsaturated alkylidene radical.

They are described in Italian Patent Application No. 19930 A/83 filed on Mar. 7, 1983 and are an object of European Patent Application No. 83201136.5 filed on Aug. 1, 1983.

Aryl-alkanoic acids are useful as anti-inflammatory, analgesic and antipyretic drugs or as intermediates for the preparation of pesticides.

Examples of arylalkanoic acids which may be prepared with the process of this invention include the compounds known as aclofenac, benoxaprofen, carprofen, diclofenac, fenclofenac, fenoprofen, flurbiprofen, indoprofen, ibuprofen, ketoprofen, naproxen, pirprofen, suprofen, tolmetin, and the like (see "USAN and the USP Dictionary of Drug Names", Mary C. Griffith Editor, The United States Pharmacopeial Convention Inc., Rockville, Md. 20852-USA).

The following examples are give to better illustrate the invention without limiting it.

EXAMPLE 1

2-(6-methoxy-2-naphthyl)-propionic acid (a) A mixture of 2-bromo-1,1-dimethoxy-1-(6-methoxy-2-naphthyl)-propane (3.39 g; 10 mmol), calcium carbonate (1 g; 10 mmol), N,N-dimethylformamide (12 g) and of water (8 g) is heated at reflux under stirring for 7 h. The mixture is cooled to 25° C., added with diethyl ether (100 ml) and the insoluble is filtered. The resulting solution is washed with water and the solvent is removed in vacuo. The residue is added with 30% sodium hydroxide aqueous solution (10 ml) and with methanol (30 ml). The reaction mixture is refluxed for 2 h and then cooled to room temperature, the mixture is diluted with water (100 ml) and extracted with diethyl ether (2×30 ml). The aqueous phase is acidified with concentrated hydrochloric acid, the insoluble is filtered, washed with water and dried at 80° C. under vacuum to give 2-(6-methoxy-2-naphthyl)-propionic acid (2.18 g; 9.5 mmol; yield 95%), m.p. 154°–155° C.

(b) A mixture of 2-bromo-1,1-dimethoxy-1-(6-methoxy-2-naphthyl)-propane (3.39 g; 10 mmol), potassium acetate (1.2 g; 12 mmol), N,N-dimethylformamide (14 ml) and of water (8 ml) is heated at 100° C. under stirring for 48 h. The reaction mixture is worked up as described in example 1a to provide 2-(6-methoxy-2-naphthyl)-propionic acid (2.23 g; 9.7 mmol; yield 97%), m.p. 155°–157° C.

(c) A mixture of 2-(1-bromoethyl)-2-(6-methoxy-2-naphthyl)-1,3-dioxolane (3.37 g; 10 mmol), potassium acetate (1.2 g; 12 mmol) and formamide (50 ml) is heated under stirring at 170° C. for 2.5 h. The reaction mixture is worked up as described in example 1a to provide 2-(6-methoxy-2-naphthyl)-propionic acid (yield 52%).

(d) A mixture of 2-(1-bromoethyl)-2-(6-methoxy-2-naphthyl)-1,3-dioxane (3.79 g; 10 mmol), potassium acetate (1.2 g; 12 mmol) and formamide (50 ml) is heated at 170° C. under stirring for 2.5 h. The reaction mixture is worked up as described in example 1a to provide 2-(6-methoxy-2-naphthyl)-propionic acid (yield 53%).

(e) A mixture of 2(1-bromoethyl)-2-(6-methoxy-2-naphthyl)-1,3-dioxolane (0.84 g; 2.5 mmol), calcium carbonate (0.3 g; 3 mmol) and formamide (5 ml) is heated at 140° C. under stirring for 1 h. The mixture is worked up as described in example 1a to provide 2-(6-methoxy-2-naphthyl)-propionic acid (0.172 g; 0.75 mmol; yield 30%), m.p. 154°–155° C.

EXAMPLE 2

2-(4-methoxyphenyl)-propionic acid (a) A mixture of 2-bromo-1,1-dimethoxy-1-(4-methoxyphenyl)-propane (3.6 g; 13 mmol), potassium acetate (2.5 g; 0.25 mmol) and formamide (25 ml) is heated at 95° C. under stirring for 6 h. The reaction mixture is worked up as described in example 1a to give 2-(4-methoxyphenyl)-propionic acid (2.2 g; 12.4 mmol; yield 96%), m.p. 56°–57° C.

(b) A mixture of 2-(bromoethyl)-2-(4-methoxyphenyl)-1,3-dioxolane (2.87 g; 10 mmol), calcium carbonate (1.2 g; 12 mmol), formamide (44 ml) and water (4 ml) is heated at 120° C., under stirring, for 6 h. The reaction mixture is worked up as described in example 1a to give 2-(4-methoxyphenyl)-propionic acid (1.67 g; 8.3 mmol; yield 83%), m.p. 55°–57° C.

(c) A mixture of 2-bromo-1,1-dimethoxy-1-(4-methoxyphenyl)-propane (2.9 g; 10 mmol), N,N-dimethylformamide (13 g), urea (6 g) and calcium carbonate (1.2 g; 12 mmol) is heated at 95° C. under stirring for 32 h. The reaction mixture is worked up as described in example 1a to give 2-(4-methoxyphenyl)-propionic acid (1.7 g; 9.2 mmol; yield 92%), m.p. 56°–57° C.

(d) A mixture of 2-bromo-1,1-dimethoxy-1-(4-methoxyphenyl)-propane (2.9 g; 10 mmol), calcium carbonate (1.2 g; 12 mmol), dimethyl sulphoxide (6 ml) and water (3 ml) is heated at 100° C. under stirring for 13 h.

The reaction mixture is worked up as described in example 1a to give 2-(4-methoxyphenyl)-propionic acid (1.8 g; 9.8 mmol; yield 98%), m.p. 56°–57° C.

(e) A mixture of 2-bromo-1,1-dimethoxy-1-(4-methoxyphenyl)-propane (2.8 g; 10 mmol), N-methylmorpholine (24 ml) and water (16 ml) is heated at 95° C., under stirring for 9 h. The reaction mixture is worked up as described in example 1a to give 2-(4-methoxyphenyl)-propionic acid (1.79 g; 9.6 mmol; yield 96%), m.p. 56°–57° C. (In this experiment, N-methylmorpholine acts as weak base as well as dipolar aprotic diluent).

(f) A mixture of 2-bromo-1,1-dimethoxy-1-(4-methoxyphenyl)-propane (0.36 g; 1.25 mmol), potassium acetate (0.15 g; 1.5 mmol) and N,N-dimethylformamide:water (6:4 v/v) (3.5 ml) is heated at 95° C. under stirring for 22 h. Usual work up gives 2-(4-methoxyphenyl)-propionic acid. 2-(1-Bromoethyl)-2-(4-methoxyphenyl)-1,3-dioxolane (0.36 g; 1.25 mmol) and 2-chloro-1,1-dimethoxy-1-(4-methoxyphenyl)-propane (0.30 g; 1.25 mmol), when reacted, separately, under the reaction conditions above described give similar results.

(g) A mixture of 2-bromo-1,1-dimethoxy-1-(4-methoxyphenyl)-propane (2.89 g; 10 mmol), potassium acetate (1.2 g; 12 mmol), N,N-dimethylformamide (12 ml) and water (8 ml) is heated at 95° C. under stirring for 16 h.

The reaction mixture is worked up as described in example 1a to give 2-(4-methoxyphenyl)-propionic acid (1.67 g; 9.3 mmol; yield 93%), m.p. 56°–57° C.

EXAMPLE 3

2-(4-isobutylphenyl)-propionic acid

A mixture of 2-(1-bromoethyl)-5,5-dimethyl-2-(4-isobutylphenyl)-1,3-dioxane (3.55 g; 10 mmol), potassium acetate (1.2 g; 12 mmol), formamide (50 ml) is heated at 170° C. under stirring for 2.5 h. The reaction mixture is worked up as described in Example 1a to give 2-(4-isobutylphenyl)-propionic acid (2.5 mmol; yield 25%), m.p. 74°–76° C.

What we claim is:

1. A process for the preparation of alpha-arylalkanoic acids which comprises the rearrangement of an alpha-chloro- (or bromo)-alkyl-arylketal in neutral or slightly alkaline conditions in the presence of a dipolar aprotic diluent selected from dimethylformamide, dimethylsulphoxide, hexamethylfosforotriamide, N-methyl-pyrrolidone, dimethylacetamide, N-methyl-morpholine, O-alkylated polyglicols, sulpholane and mixtures thereof, and of a protic substance having a high dielectric constant selected from water, urea, thiourea, formamide, acetamide, N-methyl-formamide, N-methylacetamide, N,N'-dimethyl-urea and mixtures thereof, and the subsequent hydrolysis of the thus obtained ester.

2. A process according to claim 1 wherein the rearrangement reaction is carried out at a temperature comprised between 80° and 200° C.

3. A process according to claim 1 wherein, when formamide is used as protic substance having a high dielectric constant, no dipolar aprotic diluent is used.

4. A process according to claim 1 wherein the hydrolysis of the ester is carried out by means of a base to afford a salt of alpha-arylalkanoic acid which is then treated with a mineral acid to afford the free carboxylic acid.

5. A process according to claim 1 wherein the alpha-chloro (or bromo) alkyl-arylketal starting product has the following formula

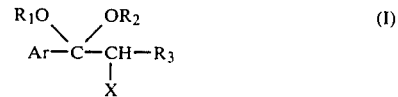

wherein

Ar is 4-methoxy-phenyl, 4-isobutyl-phenyl, 4-chlorophenyl, or 6-methoxy-2-naphthyl;

$R_1$ is methyl, $R_2$ is methyl or $R_1$ and $R_2$ together are $-CH_2-CH_2-$, $-CH_2-CH_2-CH_2-$, $-CH_2-C(CH_3)_2-CH_2-$;

$R_3$ is hydrogen or $C_1-C_6$ alkyl;

X is chlorine or bromine.

6. A process according to claim 1 wherein the alpha-arylalkanoic acid is 2-(6-methoxy-2-naphthyl)-propionic acid.

7. A process according to claim 1 wherein the alpha-arylalkanoic acid is 2-(4-methoxyphenyl)-propionic acid.

8. A process according to claim 1 wherein the alpha-arylalkanoic acid is 2-(4-isobutylphenyl)-propionic acid.

* * * * *